United States Patent [19]

Bora, Jr.

[11] 4,267,608
[45] May 19, 1981

[54] PROSTHETIC JOINT

[76] Inventor: F. William Bora, Jr., 404 Gulph Rd., Narberth, Pa. 19072

[21] Appl. No.: 948,387

[22] Filed: Oct. 4, 1978

[51] Int. Cl.³ .............................................. A61F 1/03
[52] U.S. Cl. .................... 3/1.91; 128/92 C; 403/111; 403/121; 403/291
[58] Field of Search ............ 3/1.911, 1.91, 1.9, 3/1.912, 1.913, 22; 403/121, 52, 291, 111; 128/92 C

[56] References Cited

U.S. PATENT DOCUMENTS

| | | | |
|---|---|---|---|
| 3,683,421 | 8/1972 | Martinie | 3/1.913 |
| 3,837,009 | 9/1974 | Walker | 3/1.911 |
| 3,848,276 | 11/1974 | Martinez | 128/92 C X |
| 3,864,758 | 2/1975 | Yakich | 3/1.912 X |
| 3,889,300 | 6/1975 | Smith | 3/1.91 |
| 3,934,272 | 1/1976 | Wearne et al. | 3/1.911 |
| 3,945,053 | 3/1976 | Hillberry et al. | 3/1.911 |
| 3,946,446 | 3/1976 | Schofield | 3/22 X |
| 3,969,773 | 7/1976 | Menschik | 3/22 X |
| 3,990,116 | 11/1976 | Fixel et al. | 3/1.91 |
| 3,991,425 | 11/1976 | Martin et al. | 3/1.91 |

FOREIGN PATENT DOCUMENTS 2304399  8/1974  Fed. Rep. of Germany ......... 3/1.91

Primary Examiner—Clifford D. Crowder
Attorney, Agent, or Firm—Harding, Earley & Follmer

[57] ABSTRACT

A prosthetic joint has first and second implant members opposed to each other, each having a shank for implantation in a bone of a finger, wrist, or elbow. The implant members have opposed arcuate portions that are images of each other. A pair of flexible spaced outside bands have one end secured to the first implant member and the other end secured to the second implant member with each band being wound in one direction on the arcuate portion of the first implant member and in the opposite direction on the arcuate portion of the second implant member. A central flexible band has one end secured to the first implant member and the other end secured to the second implant member with the central band being wound on the arcuate portion of the implant members in the direction opposite to the direction of wind of the outer bands.

12 Claims, 11 Drawing Figures

PROSTHETIC JOINT

BACKGROUND OF THE INVENTION

Rheumatoid arthritis is a fairly common crippling disease leading to deformity and loss of function of the joints. These effects are extremely painful and often include complete loss of function of the joints involved. If joints of the hands are involved, the afflicted patient may become totally incapable of caring for himself. Heretofore, prosthetic joints have been used to restore function to such hands. Such prosthetic joints have comprised a pair of oppositely projecting stem portions connected by a hinged center portion which bends. Typical of prior prosthetic joints is the Swanson prosthetic joint which is disclosed in U.S. Pat. No. 3,462,765.

The prior prosthetic joints may fail because of cracking or fragmentation of the stem portions or center portion due to the high forces imposed upon them incident to their bending in the hinged center portion. The prosthetic joint of the present invention handles these problems by more clearly simulating a natural finger joint and other upper extremity joints (example: wrist and elbow), and providing a prosthetic joint which offers minimal resistance and operates with very little friction since it employs a rolling action. Hence the prosthetic joint of the invention is subject to very little friction wear, has a long life, and also allows more forceful motion.

BRIEF SUMMARY OF THE INVENTION

A prosthetic joint has first and second implant members opposed to each other, each having a shank for implantation in a bone of a finger, wrist, or elbow. The implant members have opposed arcuate portions that are images of each other. Two flexible outside bands are spaced apart and have one end secured to the first implant member and the other end secured to the second member with each band being wound in one direction on the arcuate portion of the first implant member and in the opposite direction on the arcuate portion of the second implant member. A central flexible band situated between the outside bands has one end secured to the first implant member and the other end secured to the second implant member with central band being wound on the arcuate portion of the implant members in the direction opposite to the direction of wind of the two outer bands. While the system of two outer and one central band provides considerable lateral stability, greater lateral stability can be provided by a tongue and groove arrangement.

DETAILED DESCRIPTION

Figure 1:
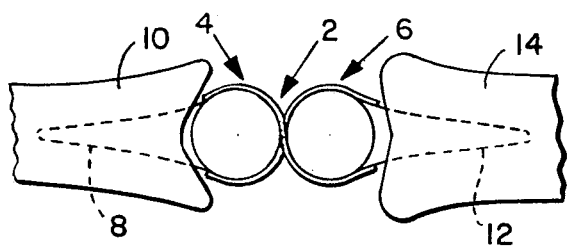
FIG. 1 is a side elevation partially broken away of a proximal interphalangeal joint.

A prosthetic joint 2 in accordance with the invention is shown in FIG. 1, and has a first implant member 4 and a second implant member 6 which oppose each other. Implant member 4 has a shank 8 implanted in a middle phalanx 10, and implant member 6 has a shank 12 implanted in a proximal phalanx 14.

Figure 3:
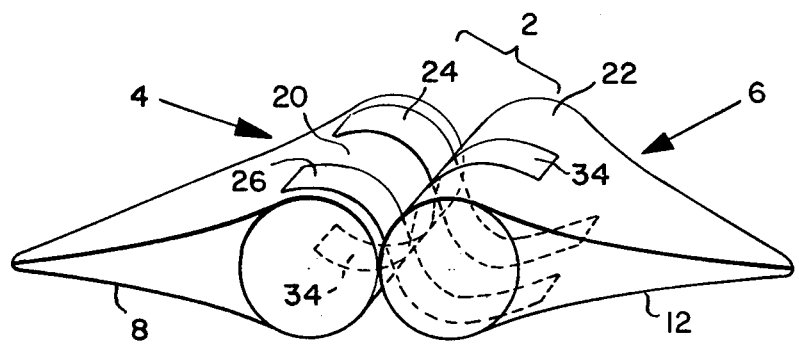
FIG. 3 is a side perspective view of the joint of FIG. 1.

As best seen in FIG. 3, implant members 4 and 6 have arcuate portions 20 and 22 respectively which are images of each other having equal radii. A pair of spaced flexible outer bands 24 and 26 are each secured at one end to arcuate portion 20 by adhesive or other suitable means. Bands 24 and 26 are wound clockwise about arcuate portion 20 and then counterclockwise about arcuate portion 22 to which their other ends are each secured. A central flexible band 34 has an end secured to arcuate portion 22 and is wound counterclockwise about arcuate portion 22 as viewed in FIG. 3, and then is wound clockwise about arcuate portion 20 to which its other end is secured. Each of bands 24, 26 and 34 is in simultaneous contact with both arcuate portions 20 and 22 in a plane passing through the axes of arcuate portions 20 and 22, that is to say where the arcuate portions 20 and 22 are closest to each other.

Implant members 4 and 6 may be made of any of the materials heretofore used to make prosthetic joints, for example, a metal such as stainless steel, or a plastic, for example, a polyalkylene resin such as polyethylene and polypropylene, a polyurethane resin or silicone rubber. Likewise the bands may be made of a wide variety of materials, for example, silicone rubber, spring steel and polyurethane, and may be reinforced with Dacron polyester. While the arcuate portions of the joints and their associated shanks may be all of the same material, it is also practical to have the arcuate portions of one material, for example, of metal, and the shanks of a different material, for example, of plastic. Such a combination is advantageous when it is desired to have a very hard surface for the arcuate portions and yet have some flexibility in the shanks. A segmented polyurethane is preferred for use in the arcuate portions, shanks and bands. Such a polyurethane is available from Upjohn (555 Alaska Ave., Torrance, Calif. 90503) and is available in a wide range of hardness, for example, Shore D 55 which is suitable for the arcuate portions and shanks and a Shore A 74-80 which is suitable for the bands. For suitable materials, reference may be had to "Concise Guide To Biomedical Polymers" published in 1973 by Charles Thomas, "Polymers In Medicine And Surgery" published by Plenum Press in 1975 and "Segmented Polyurethane" by Boretos and Pierce in J. Biomed. Mat. Res. 2:121; 1978 which are incorporated herein by reference. Where plastics are used, they may be reinforced with a fabric of, for example, a polyester fiber such as duPont's Dacron.

The bands 24, 26, 34, may be secured to the arcuate portions 20, 22 by mechanical means, by an adhesive, by heat welding, by chemical bonding, by injection molding, or other suitable means. The bands are of a resilient material and are under tension to urge implant members 8 and 12 together.

Figure 2:
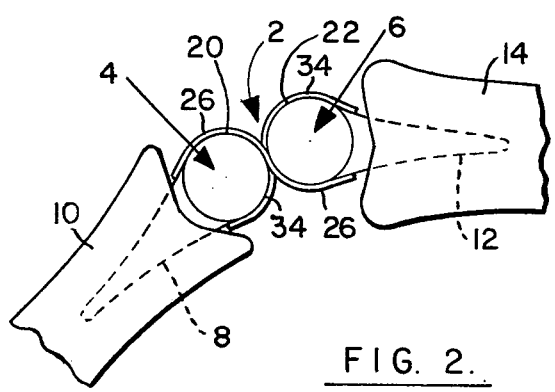
FIG. 2 is a side elevation of the joint of FIG. 1 with the middle phalanx in flexure about 45°.

Adverting to FIG. 2, it will be seen that when the proximal phalanx 10 is moved downwardly in flexion, arcuate portion 20 rolls along bands 24, 26 and 34 on arcuate portion 22 with bands 24 and 26 unwinding from arcuate portion 22 onto arcuate portion 20 and with band 34 unwinding from arcuate portion 20 and onto arcuate portion 22. The bands 24, 26 and 34 function to keep implant members 4 and 6 together while permitting them to roll about each other forming the desired joint action in flexion. It will be noted that as implant member 4 rolls about implant member 6 the movement of implant member 4 about the axis of the arcuate portion 22 is one-half the amount of rotation of arcuate portion 20 about its own axis.

Figure 5:
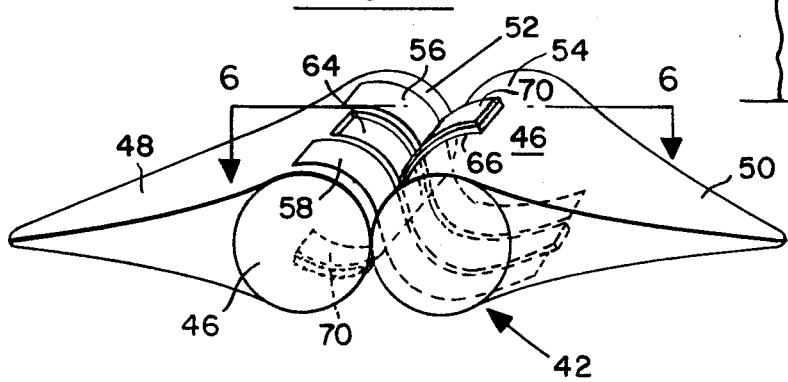
FIG. 5 is a side perspective view of a modified prosthetic joint having a tongue and groove in the arcuate portion of its implant members.
Figure 6:
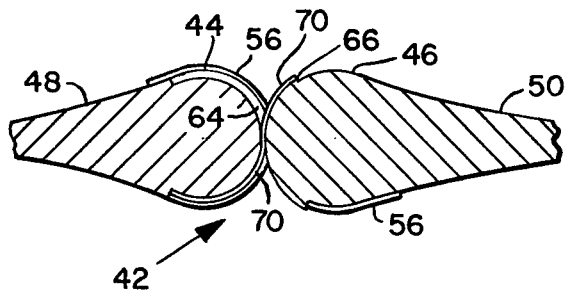
FIG. 6 is a vertical section taken on the plane indicated by the lines 6—6 in FIG. 5.

An alternative prosthetic finger joint 42 is shown in FIGS. 5 and 6. Prosthetic joint 42 is very similar to prosthetic joint 2 having implant members 44 and 46 having respectively shanks 48 and 50 for implantation and respectively having image arcuate portions 52 and 54. Spaced flexible outer bands 56 and 58 are wound clockwise on implant member 44 and counterclockwise on implant member 46, each having their ends respectively secured to members 44 and 46. Prosthetic joint 42 differs from prosthetic joint 2 in having an arcuate central groove 64 in arcuate portion 52 and a registering arcuate central tongue 66 on arcuate portion 54 engaged in groove 64. A flexible central band 70 is wound counterclockwise, as viewed in FIG. 5, about tongue 66 and thence clockwise in groove 64, the ends of band 70 being secured by adhesive, pressure heat or by chemically bonding to the groove 64 and tongue 66. All of bands 56, 58 and 70 are of resilient material such as silicone rubber or a urethane elastomer (for example Upjohn's PELLETHANE) and under tension to urge implant members 44 and 46 together.

It will be readily apparent that the operation of prosthetic joint 42 is the same as the operation of prosthetic joint 2 but that the continuous engagement of tongue 66 in groove 64 as members 44 and 46 rotate relative to one another provides added lateral stability to the prosthetic joint.

Figure 7:
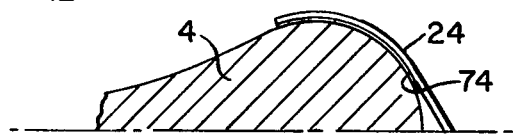
FIG. 7 is a sectional view partially broken away showing one of the means for attaching a band.
Figure 4:
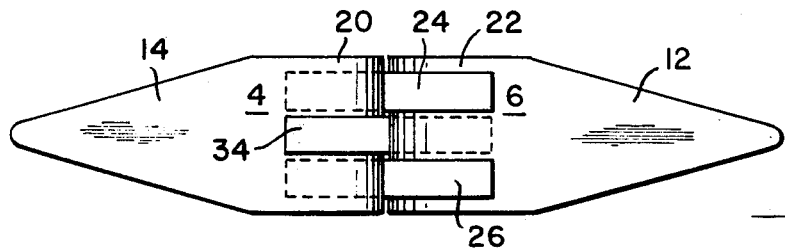
FIG. 4 is a bottom plan view of the joint of FIG. 1.
Figure 8:
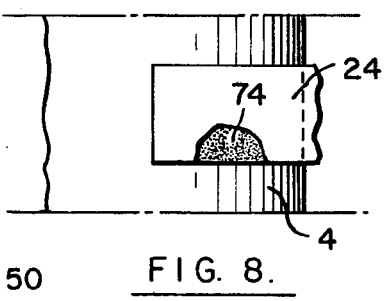
FIG. 8 is a top plan view of the structure of FIG. 7.

As shown in FIGS. 7 and 8, band 24 may be attached to member 4 by an adhesive 74.

Figure 9:
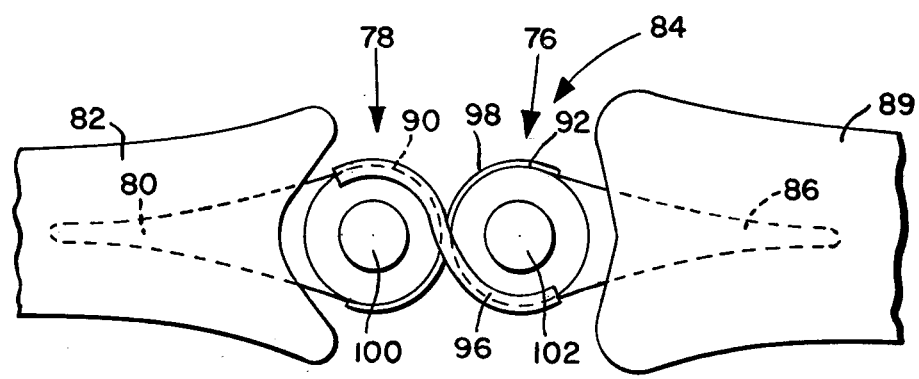
FIG. 9 is a side elevation view of a modified prosthetic joint having an oval-like arcuate portion that provides for lateral movement.
Figure 10:
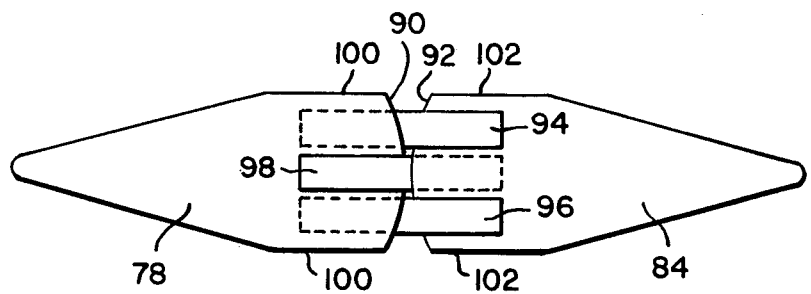
FIG. 10 is a bottom plan view of the prosthetic joint of FIG. 9.

Turning now to the alternative embodiment of the invention shown in FIGS. 9 and 10, there is shown a prosthetic joint 76 comprising a first implant member 78 having a shank 80 implanted in a bone 82, and an opposing second implant member 84 having a shank 86 implanted in a bone 89, with prosthetic joint 76 being a substitute for a normal metacarpalphalangeal joint, for example.

The first implant member 78 has an arcuate portion 90 that opposes arcuate portion 92 of second implant member 84.

Outer flexible bands 94, 96 have one end secured to first implant member 78 and the other end secured to second implant member 84 with the bands being wound clockwise on arcuate portion 90 of the first implant member 78 and being wound counterclockwise on the arcuate portion 92 of second implant member 84. A central flexible band 98 has one end secured to arcuate portion 90 of first implant member 78 and the other end secured to arcuate portion 92 of second implant member 84, with central band 98 being wound in a direction opposite to the direction of wind of the outer bands. The bands are resilient and under tension and urge the implant members 78 and 84 together.

The operation of prosthetic joint 76 is the same as the operation of prosthetic joints 2 and 42, except that prosthetic joint 76 is provided with means for permitting limited lateral movement of the prosthetic joint, said means comprising arcuate portions 90, 92 that curve away from each other at their ends 100, 102.

Prosthetic joint 76 is particularly useful in finger and wrist joints where limited lateral movement is desirable, and prosthetic joint 42 is particularly adapted for elbow joints where limited lateral mobility or movement is undesirable.

Figure 11:
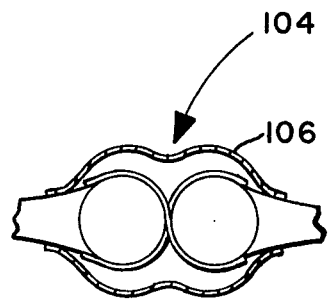
FIG. 11 is a side elevation view of a modified prosthetic joint having an encapsulation membrane covering the central portion of the joint.

Another alternative prosthetic finger joint 104 is shown in FIG. 11. This alternative design has an encapsulation membrane 106 which may be used with any of the previously described embodiments of the invention. As shown in FIG. 11, encapsulation membrane 106 encapsulates the bands and arcuate portions of the implant members. Encapsulation membrane 106 may be of a similar material or a material compatible with the shanks and arcuate portions of the implant members. Encapsulation membrane 106 prevents the ingrowth of fibrohlasts between the rollers thereby producing scar tissue which could compromise joint motion.

The prosthetic joint of this invention has many advantages over the prior art devices. For example, it may allow ease of flexion while maintaining forces that assist extension. This increased ease of flexion is achieved with minimal resistance and allows increased flexion power, a definite advantage where muscle power is affected by a disease such as rheumatoid arthritis.

Also, by altering the shape of the implant members as in prosthetic joint 76, or by changing the tightness of the connecting flexible bands, motion in a lateral plane can be preset. Tight bands permit little lateral motion while loose bands permit a little lateral motion. Implant members having arcuate portions that do not curve away from each other at their ends permit little or no lateral motion, while implant members having arcuate portions that curve away from each other at their ends permit more lateral motion.

The prosthetic joint of this invention allows the patient to bend (flex) the joint, and assists in extension in a positive manner because the normal position of the prosthetic joint is in extension as shown in FIGS. 1 and 3, for example.

I claim:

1. A prosthetic joint for a finger, wrist or elbow comprising:

first and second implant members opposed to each other, each implant member having a shank for implantation in a bone of a finger, wrist or elbow, each implant member having opposed substantially cylindrical arcuate portions, a first flexible band having one end secured to the first implant member and the other end secured to the second implant member with the band being wound in one direction on the arcuate portion of the first implant member and in the opposite direction on the arcuate portion of the second implant member, and a second flexible band having one end secured to the first implant member and the other end secured to the second implant member, the second band being wound on the arcuate portion of the first implant member in the direction opposite to the direction of wind of the first band and being wound on the arcuate portion of the second implant member in the direction opposite to the direction of wind of the first band, said band being of resilient material and under tension to urge implant members together and being so tensioned that the extension position is the normal position of the joint, said bands remaining in contact with said arcuate portions at all times during extension and flexion.

2. The prosthetic joint in accordance with claim 1, including interengaging means for limiting the relative lateral movement of the implant members.

3. The prosthetic joint in accordance with claim 1, including means encapsulating a portion of the arcuate portions of the implant member to prevent scar tissue from forming between said arcuate portions and restricting the flexing of the joint.

4. The prosthetic joint in accordance with claim 1, including:
a third flexible band in parallel with the first band,
said second band lying between the first and third bands and forming a central band with the first and third bands forming outer bands, and
all of the bands being resilient and under tension and urging the implant members toward each other,
said bands being so tensioned that the extension position is the normal position of the joint.

5. The prosthetic joint of claim 4, including interengaging tongue and groove means in the arcuate portions of the implant members for limiting the lateral movement of the implant members.

6. The prosthetic joint in accordance with claim 1 having a third flexible band in parallel with the first band.

7. The prosthetic joint in accordance with claim 6 in which the second band lies between the first and third bands and forms a central band between the first and third bands.

8. The prosthetic joint in accordance with claims 1, 6 or 7 in which at least one of the bands is resilient and under tension.

9. A prosthetic joint comprising:
first and second implant members opposed to each other,
each implant member having a shank for implantation in a bone,
each implant member having opposed substantially cylindrical arcuate portions,
said arcuate portions having lateral ends,
a first flexible band having one end secured to the first implant member and the other end secured to the second implant member with the band being wound in one direction on the arcuate portion of the first implant member and in the opposite direction on the arcuate portion of the second implant member, and
a second flexible band having one end secured to the first implant member and the other end secured to the second implant member, the second band being wound on the arcuate portion of the first implant member in the direction opposite to the direction of wind of the first band and being wound on the arcuate portion of the second implant member in the direction opposite to the direction of wind of the first band,
including means for permitting lateral movement of the prosthetic joint,
said means comprising implant members having arcuate portions that are convex and curve away from each other at their lateral ends.

10. A prosthetic joint comprising:
first and second implant members opposed to each other,
each implant member having a shank for implantation in a bone,
each implant member having opposed substantially cylindrical arcuate portions,
said arcuate portions having lateral ends,
a first flexible band having one end secured to the first implant member and the other end secured to the second implant member with the band being wound in one direction on the arcuate portion of the first implant member and in the opposite direction on the arcuate portion of the second implant member,
a second flexible band having one end secured to the first implant member and the other end secured to the second implant member, the second band being wound on the arcuate portion of the first implant member in the direction opposite to the direction of wind of the first band and being wound on the arcuate portion of the second implant member in the direction opposite to the direction of wind of the first band,
a third flexible band in parallel with the first band,
said second band lying between the first and third bands and forming a central band with the first and third bands forming outer bands,
all of the bands being resilient and under tension and urging the implant members toward each other,
said bands being so tensioned that the extension position is the normal position of the joint,
including means for permitting lateral movement of the prosthetic joint,
said means comprising implant members having arcuate portions that are convex and curve away from each other at their lateral ends,
whereby the prosthetic joint is especially adapted for use as a finger joint.

11. A prosthetic joint for a finger, wrist or elbow comprising:
first and second implant members opposed to each other,
each implant member having a shank for implantation in a bone of a finger, wrist or elbow,
each implant member having opposed substantially cylindrical arcuate portions that are images of each other,
two flexible outside bands spaced apart with each outside band having one end secured to the first implant member and the other end secured to the second implant member with each outside band being wound in one direction on the arcuate portion of the first implant member and in the opposite direction on the arcuate portion of the second implant member, and
a central flexible band situated between the outside bands and having one end secured to the first implant member and the other end secured to the second implant member, the central band being wound on the arcuate portion of the first implant member in the direction opposite to the direction of wind of the two outside bands, each of the bands being in simultaneous contact with both arcuate portions in a plane which passes through the axes of the arcuate portions, said bands being of resilient material and under tension to urge the implant members together and being so tensioned that the extension position is the normal position of the joint, said bands remaining in contact with said arcuate portions during flexion, said first implant member being adapted for movement in flexion, its arcuate portion rolling along the bands on the arcuate portions of the second implant member with the outside bands unwinding from the arcuate portion of the second implant member onto the arcuate portion of the first implant member and the central band unwinding from the arcuate portion of the first implant member onto the arcuate portion of the second implant member, said bands keeping the arcuate sections together while permitting them to roll about each other to flex the joint, the normal position of the joint being in extension to assist extension in a positive manner and yet allow ease of flexion with minimal resistance.

12. The prosthetic joint of claim 11, said arcuate portions being of a hard material relative to the shanks and the shanks being of a more flexible material relative to the arcuate portions to allow for some flexibility in the shanks.

* * * * *